US00PP28927P3

(12) United States Plant Patent
Olesen

(10) Patent No.: US PP28,927 P3
(45) Date of Patent: Feb. 6, 2018

(54) HYBRID TEA ROSE PLANT NAMED 'POULHT010'

(50) Latin Name: ***Rosa* hybrid**
Varietal Denomination: Poulht010

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 106 days.

(21) Appl. No.: 14/756,278

(22) Filed: Aug. 20, 2015

(65) Prior Publication Data

US 2017/0055393 P1 Feb. 23, 2017

(51) Int. Cl.
*A01H 5/02* (2006.01)

(52) U.S. Cl.
USPC ..... Plt./135

(58) Field of Classification Search
USPC ..... Plt./101, 130, 135
See application file for complete search history.

(56) References Cited

PUBLICATIONS

Poulsen Roser A/S website. http://www.poulsenroser.com/assortment/rose-collections/hybrid-tea-poulsen/bollywood.aspx. Accessed Mar. 16, 2017. 1 page.*

* cited by examiner

*Primary Examiner* — Susan McCormick Ewoldt
*Assistant Examiner* — Karen Redden

(57) ABSTRACT

A new garden rose plant of the Hybrid Tea class which has abundant, orange blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulht010'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 1999 and the resulting seeds were planted in a controlled environment in Fredensborg, Denmark. The new variety, named 'Poulht010', originated as a single seedling from the stated cross.

The new variety may be distinguished from its male pollen parent and female seed parent primarily by the following characteristics. The female parent, an unnamed and non-patented seedling, has medium yellow flowers, while the newly claimed variety has orange blend flowers. The male pollen parent, an unnamed and non-patented seedling, has medium red flowers, while the newly claimed variety has orange blend flowers.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulht010' from all other varieties of which we are aware.

As part of the rose development program, Mogens N. Olesen germinated the seeds from the aforementioned hybridization during winter of 1999 and conducted evaluations on the resulting seedlings in a controlled environment in Fredensborg, Denmark. 'Poulht010' was selected in the spring of 2000 by the inventor as a single plant from the progeny of the aforementioned hybridization.

Asexual reproduction of 'Poulht010' by traditional budding and rooted cuttings was first done by Mogens N. Olesen in the nursery in Fredensborg, Denmark in July, 2000. This initial and other subsequent asexual propagations conducted in controlled environments have demonstrated that the characteristics of 'Poulht010' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulht010'.

Specifically illustrated in FIG. 1 of the drawings are open flowers, flower petals detached, reproductive flower parts, and sepals detached.

Figure 1:
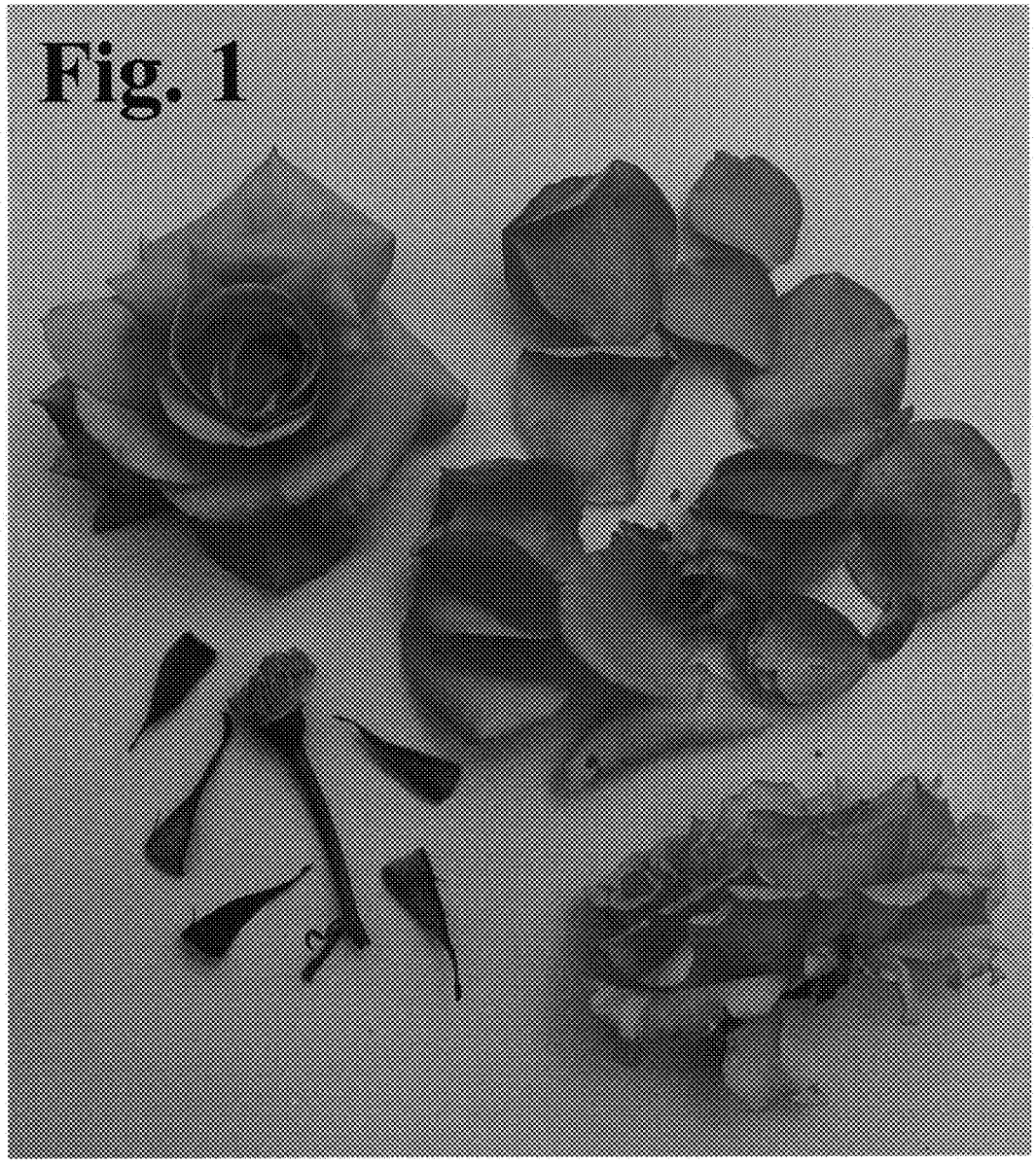
Figure 2:
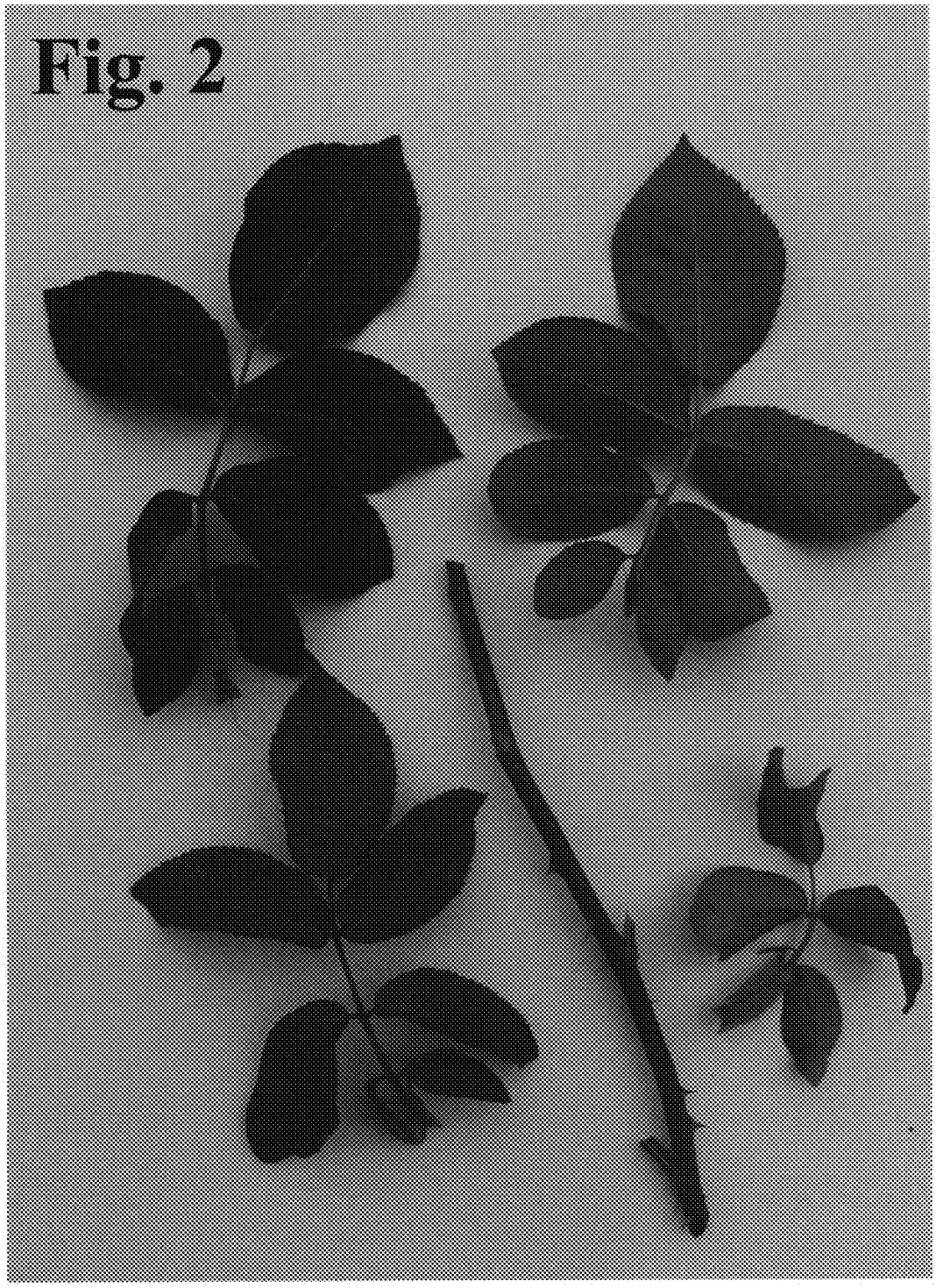

Specifically illustrated in FIG. 2 of the drawings are mature and juvenile leaves, and a bare stem. Plants shown are 2 years of age.

DETAILED DESCRIPTION OF THE VARIETY

The following is a description of 'Poulht010', as observed in its growth in in a field nursery in Marion County, Oreg.

Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulrim', U.S. Plant Pat. No. 12,465 are compared to 'Poulht010' in Chart 1.

CHART 1

| | 'Poulht010' | 'Poulrim' |
|---|---|---|
| Petal Count | 60 | 25 to 30 |
| Flower Diameter | 110 mm | 100 to 120 mm |
| General Tonality of Flower Color | Yellow-Orange Group 18A | Blend of Greyed-Orange 170C, Orange 29A with intonations of Red Group 39A |

FLOWER AND FLOWER BUD

Blooming habit: Continuous.

Flower bud:

*Size.*—Upon opening, 35 mm in length from base of receptacle to end of bud. Bud diameter is 16 mm.

*Bud form.*—Ovoid.

*Bud color.*—As sepals divide petals are Yellow-Orange Group 18B with intonations of Red Group 37B.

*Sepal inner surface.*—Color: Yellow-Green Group 147C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—40 mm long, 10 mm wide.

*Receptacle.*—Texture: Smooth. Size: 9 mm in height, 11 mm wide. Color: Yellow-Green Group 144A. Shape: Campanulate.

*Pedicel.*—Surface: Smooth. Length: 40 mm. Diameter: 3 mm on average. Color: Yellow-Green Group 144A. Strength: Strong.

Flower bud development: Flower buds are borne singly and in clusters of 3 to 5 flower buds per stem.

Flower bloom:

*Fragrance.*—Moderate floral perfume.

*Duration.*—The blooms have a duration on the plant of approximately 14 days. Petals fall cleanly away from plant after flowers have fully matured.

*Size.*—Flower diameter is 110 mm when open. Flower depth is 35 mm.

*Flower shape.*—High centered, double, with a high pointed center which is tightly closed.

*Shape of flower, side view.*—The upper portion is convex. The lower portion is concave.

Petalage: Under normal conditions, flowers have 60 petals total, 10 of which are petaloids.

General tonality of flower: Open flowers are Yellow-Orange Group 18A. Mature flowers become Yellow-Orange Group 16D.

Petal color:

*Upon and after opening, outer petals.*—Upper surface: Generally Yellow-Orange Group 14C. The marginal zone is Orange Group 28D. At the base of the petal Yellow Group 6A. Lower surface: Orange-Red Group 35C splashed with Yellow-Orange Group 18B. The petal zone is colored Yellow Group 8A.

*Upon and after opening, inner petals.*—Upper surface: Yellow-Orange Group 13B with marginal intonations of Orange Group 28D. The basal zone is Yellow Group 6A. Lower surface: Orange Group 35B splashed with Yellow-Orange Group 18B. Yellow Group 8A at the basal zone.

Petals:

*Petal reflex.*—Strong.

*Margin.*—Entire with an occasional cleft. Strong undulations.

*Shape.*—Generally broad elliptical. Apex shape: Rounded. Base shape: Broadly acute.

*Size.*—45 mm (l)×55 mm (w).

*Texture.*—Smooth.

*Thickness.*—Average.

Petaloids:

*Size.*—12 mm (l) by 8 mm (w).

*Quantity.*—About 10.

*Shape.*—Irregular.

*Color.*—Yellow-Orange Group 13B blended with Orange Group 28D on the upper surface. The lower surface is Orange Group 35B splashed with Yellow-Orange Group 18B.

Reproductive flower parts:

*Pollen.*—None observed.

*Anthers.*—Size: 2 mm in length. Color: Yellow-Orange Group 19B. Quantity: 40 on average.

*Filaments.*—Color: Yellow Group 8B. Length: 10 mm.

*Pistils.*—Length: 9 mm. Quantity: 35 on average.

*Stigmas.*—Color: Yellow-White Group 158C.

*Styles.*—Color: Red-Purple Group 62C.

*Location of stigmas.*—Inferior in location relative to the length of the filaments and the height of the anthers.

*Hips.*—None Observed.

PLANT

Plant growth: Upright, bushy. Plants are 90 cm in height, and 80 cm wide.

Stems:

*Color.*—Juvenile growth: Yellow-Green Group 144B. Mature growth: Yellow-Green Group 144A.

*Length.*—On average, canes are 50 cm from the base of the plant to the flowering portion.

*Diameter.*—About 8 mm.

*Internodes.*—On mature canes about 50 mm between nodes.

*Surface texture.*—Young wood: Smooth. Older wood: Smooth.

Long prickles:

*Incidence.*—4 prickles per 10 cm of stem.

*Size.*—Average length of prickles on mature stems is 4 mm.

*Shape.*—Upper portion is linear. Lower portion is concave.

*Color.*—Juvenile prickles: Yellow-Green Group 152D. Mature prickles: Yellow-Green Group 152D.

Plant foliage:

*Compound leaf.*—180 mm (l)×35 (w).

*Quantity.*—2 leaves per 10 cm of stem on average.

*Color of juvenile foliage.*—Upper side: Yellow-Green Group 144A with marginal intonations of Greyed- Red Group 180B. Lower side: Yellow-Green Group 144A with marginal intonations of Greyed-Red Group 180B.

*Color of mature foliage*.—Upper side: Yellow-Green Group 147A. Lower side: Yellow-Green Group 147B.

Plant leaves and leaflets:

*Stipules*.—Size: 30 mm long, 6 mm wide. Quantity: 2 per compound leaf. Shape: Linear, slightly broad based with outward extending apices. Margins: Finely serrated. Color:.

*Petiole*.—Length: 50 mm. Diameter: 1.5 mm.

*Upper surface*.—Color: Yellow-Green Group 144A.

*Lower surface*.—Color: Yellow-Green Group 144A.

*Rachis*.—Length: 50 mm. Upper surface: Color: Yellow-Green Group 144A.

Lower surface.—Color: Yellow-Green Group 144A. Observations: Small prickles.

*Leaflet*.—Quantity: Normally 7 leaflets. Margins: Serrated. Size: On average terminal leaflets are 80 mm long, mm 55 wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Hybrid Tea rose class named 'Poulht010', substantially as illustrated and described herein, due to its abundant orange blend flowers, disease resistance, and extended period of bloom.

* * * * *